United States Patent [19]

Morrisroe et al.

[11] 4,101,589

[45] Jul. 18, 1978

[54] 1,3,4-TRIOLS AND DERIVATIVES THEREOF

[75] Inventors: John J. Morrisroe, Whittier; Thomas F. Banigan, Arcadia, both of Calif.

[73] Assignee: Pilot Chemical Company, Santa Fe Springs, Calif.

[21] Appl. No.: 421,427

[22] Filed: Dec. 3, 1973

Related U.S. Application Data

[60] Division of Ser. No. 135,427, Apr. 19, 1971, Pat. No. 3,778,482, which is a continuation-in-part of Ser. No. 687,137, Dec. 1, 1967, abandoned, which is a continuation-in-part of Ser. No. 618,824, Feb. 27, 1967, Pat. No. 3,544,603.

[51] Int. Cl.$^2$ ............................ C07C 43/11; C07C 41/02
[52] U.S. Cl. ................................ 260/615 B; 252/170
[58] Field of Search ................................ 260/615 B

[56] References Cited

U.S. PATENT DOCUMENTS

| | | | |
|---|---|---|---|
| 2,706,207 | 4/1955 | Schnell et al. | 260/615 B |
| 3,406,208 | 10/1968 | Blaser et al. | 260/615 B |
| 3,445,525 | 5/1969 | Bormann et al. | 260/615 B |
| 3,449,318 | 6/1969 | Roth et al. | 260/615 B X |
| 3,595,924 | 7/1971 | Kaloplissis et al. | 260/615 B |
| 3,778,479 | 12/1973 | Morrisroe et al. | 260/615 B |

*Primary Examiner*—Howard T. Mars
*Attorney, Agent, or Firm*—Lyon & Lyon

[57] ABSTRACT

Described herein is a novel class of compounds of formula

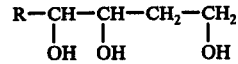

where R is a hydrogen or linear alkyl group of from 1 to about 11 carbon atoms. The compounds are prepared by dihydroxylation of a 3-alken-1-ol, e.g., by peroxidation in formic acid to the Formate ester which latter is hydrolyzed to the 1,3,4-triol of the invention. The multifunctional compounds can be converted to surfactants, emulsifiers and lubricants, and are useful in the formation of urethanes and alkyd-type resins.

7 Claims, No Drawings

1,3,4 TRIOLS AND DERIVATIVES THEREOF

CROSS REFERENCE TO RELATED APPLICATIONS

This application is a division of of our co-pending application Ser. No. 135,427, filed Apr. 19, 1971, now U.S. Pat. No. 3,778,482 which was in turn a continuation-in-part of our copending application Ser. No. 687,137 filed Dec. 1, 11967, and now abandoned which was in turn a continuation-in-part of our copending application Ser. No. 618,824 filed Feb. 27, 1967, (now U.S. Pat. No. 3,544,603). The subject matter of this application is related to that of our applications Ser. No. 84,226 (now abandoned) and 84,161, each filed Oct. 26, 1970 as continuations-in-part of said application Ser. No. 618,824, and to our U.S. Pat. No. 3,778,479.

BRIEF SUMMARY OF THE INVENTION

By this invention there is provided a novel class of compounds represented by the formula:

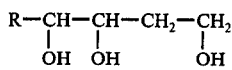

where R is hydrogen or $C_1$ - $C_{11}$ linear alkyl. Also provided are ethoxylates of the above 1,3,4-triols, whose ethoxyl groups depend from plural carbons of the parent compound.

DETAILED DESCRIPTION OF THE INVENTION

The 3-alken-1-ols which are the precursors to the compounds of the invention are obtained by the reaction of linear alpha olefins with formaldehyde at elevated temperatures, all as described in our aforesaid U.S. Pat. No. 3,778,479, the disclosure of which is incorporated herein by reference.

Briefly, the 3-alken-1-ol precursors are obtained by reacting linear alpha olefins of from 3 to about 14 carbon atoms with formaldehyde at temperatures preferably from about 180° to about 250° C. Most preferably, reaction temperature is from about 210° to about 250° C. Of course, instead of formaldehyde any substance which decomposes under the reaction conditions to yield formaldehyde can be employed, e.g., paraformaldehyde, trioxymethylene and isomers thereof, etc. The reaction can be carried out over a wide range of olefin to aldehyde mole ratios, but preferably is carried out at olefin aldehyde mole ratios between about 2/1 and 0.5/1.

The olefin-aldehyde reaction may be carried out in the presence of an organic acid containing from about 1 to 6 carbon atoms, e.g., formic acid, propionic, n-butyric and acetic acid. Acetic acid is preferred and may be used as an acetic acid-acid anhydride mixture. The acid forms an ester with the resulting alcohol so that hydrolysis of the ester to the alcohol is desirable in final work-up of the product alkenol.

The 1,3,4-triols of the invention can be produced from the 3-alken-1-ols by adaptation of the peroxidation procedure described in D. Swern et al, "Hydroxylation of Monounsaturated Fatty Materials", J. Am Chem. Soc. 67, 1786 (1945), e.g.:

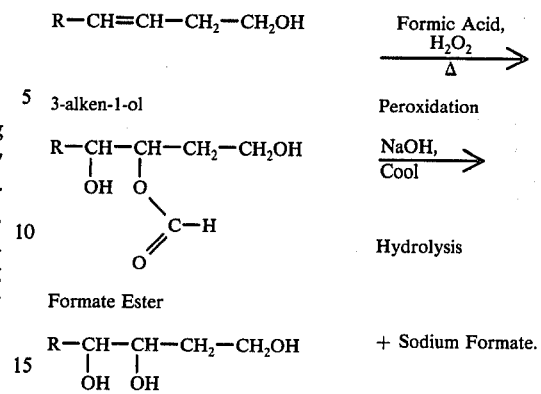

Of course, a diformate ester may form instead, although the second ester linkage is relatively unstable and, if formed, is believed but transient. Any low molecular weight organic acid can be used, although formic acid is preferred. When formic acid is employed in the peroxidation step, temperature should be maintained in the range of about 35° to about 50° C., preferably between about 40° to about 45° C.

While the homologs of the 1,3,4-triol series from R = H to R = n-undecanyl are white, crystalline solids the lower members are water soluble, high melting (>200° C.) and salt-like in appearance whereas the higher members, e.g., the tridecane- and pentadecane triols are water insoluble, possess lower melting points, and occur as waxy crystals melting at or about 90° C.

The 1,3,4-triols of the invention differ markedly in their properties from closely related analogs. Thus, for example, 1,3,4-tridecanetriol is greatly superior from the standpoint of detergency to 1,2,3-dodecanetriol. Again, 1,3,4-butanetriol is a white, salt-like crystalline solid which melts at about 200° C. and reacts with phthalic anhydride to form a white crystalline solid of melting point 75° C. Glycerol (1,2,3-propanetriol), on the other hand, is a colorless, viscous liquid which melts at about 18° C. and reacts with phthalic anhydride to form an alkyd resin.

The higher 1,3,4-triols, e.g., tridecanetriol and pentadecanetriol absorb many times their weight in water, swelling into an opalescent stiff paste exhibiting good emollient and vanishing properties on the skin. Members of the series from at least about R = n-pentyl to R = n-nonyl exhibit surface active and detergent properties which are maximized at about 1,3,4-undecanetriol.

The compounds of the invention undergo the reactions expected of polyhydric aliphatics. Thus, they can be converted to monoesters of olefinic and hydroxy fatty acids, useful as emulsifiers; to triesters, useful as synthetic lubricants; to urethanes, useful for decorative coatings and flexible and rigid plastic foams, and to alkyd-type resins useful as vanish and paint vehicles. The ability to vary the length of the R group is desirable as it permits various degrees of internal plasticization in resinous products and variation of lipophilic character in detergent products. 1,3,4-nonanetriol has proved especially versatile as an intermediate in organic synthesis because of its solubility in water as well as various organic solvents (acetone, methanol, pyridine).

The 1,3,4-triols can be converted into ethylene oxide adducts useful as nonionic surfactants by ethoxylation in conventional manners, ie., reaction with sodium methylate, sodium hydroxide or sodium metal in an inert atmosphere followed by exposure to ethylene oxide, e.g., bubbled through the liquid at elevated temperatures. Alternatively, acid catalysts such as sulfuric or phosphoric acid may be used. The degree of ethoxylation can be controlled by the amount of ethylene oxide which is added. Thus, a 2 – 4 mole, 5 – 8 mole or even up to 20 mole ethoxylate can be formed. The preferred range is from about 2 to 8 moles. Typical ethoxylation temperatures are from about 125° to about 225° C. or more when the reaction is carried out at atmospheric pressures. At higher pressure, of course, lower temperature can be employed. At lower temperatures undesirable side reactions are less likely to occur. It will be appreciated that ethoxylation occurs at multiple locations along the 1,3,4-triol, due to the presence of plural hydroxyl groups. Thus, for example, one species produced by ethoxylation might be represented as:

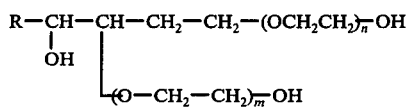

when $m$ and $n$ are integers totaling from 2 to 20, etc. Again, ethoxylation may occur through all three hydroxyls of the triol. In any case, as noted above, the overall degree of ethoxylation can be controlled by controlling the amount of ethylene oxide added.

The invention is further described and illustrated by the following examples, in which all parts and percentages are by weight and all temperatures °C. unless otherwise qualified.

EXAMPLE 1

This example illustrates the production of 1,3,4-tridecanetriol. Thirty percent hydrogen peroxide (0.35 mole) was added to a stirred solution of 3-tridecen-1-ol (0.25 mole) in formic acid at a rate to maintain a reaction temperature of 40°-50° C. Following the exotherm this temperature was maintained by external heating for a total reaction time of about 2 hours. During this period the initially two-phased system clarified into a single clear phase.

The crude triol was readily isolated (as a formate ester) by drowning the reaction mixture in water. Alternatively, excess peroxide was reduced with bisulfite ion and the formic acid was distilled from the reaction mixture for recycle before drowning. The crude formate ester was then converted to crude triol by saponification with 30% caustic soda at a temperature kept below about 45° C followed by drowning and water washing. After recrystallization using acetone, the pure triol was obtained (80% yield) as white waxy crystals having a melting point of 88.5° – 90° C, hydroxyl number of 692, percent carbon 67.16 and percent hydrogen 12.03. Infrared spectroscopy (thin film and mull) showed no absorption peaks attributable to double bonds but prominent peaks associated with hydroxyl stretch (3.1$\mu$) and primary and secondary hydroxyl groups (9–11.5 $\mu$). Further evidence of compound identity and purity were observed by vapor phase chromatography.

EXAMPLE 2

The detergent properties of the 1,3,4-triol of Example 1 are compared to those of 1,2,3-dodecanetriol (also known as $\alpha$-nonylglycerol). The latter triol was made in about 90% yield by treatment of 2-dodecen-1-ol (0.0815 mole) from SeO$_2$ oxidation of 1-dodecene with 30% hydrogen peroxide (0.10 mole) in 90% formic acid. The reaction required about 3 hours at 40°-43° C. Drowning of the reaction mixture in water yielded the product as a formate ester which was converted to the crude triol by careful saponification (under 45° C.) with 30% caustic soda followed by further drowning and cold water washing. After several acetone recrystallizations the $\alpha$-nonylglycerol was obtained as white waxy flakes, m.p. 80° C.; hydroxyl number 752 (theor. 773). An infrared spectrum showed strong absorption bands in regions specific to primary and secondary hydroxyl groups and to triols. This triol can also be recrystallized from hot water.

The two compounds were evaluated for dishwashing performance according to the following procedure. Into a three-quart mixing bowl in a constant temperature bath at 45° C. was placed 250 milliliters of water containing 150 pm calcium carbonate. Five milliliters of a sample of solution prepared by mixing 15 grams of sample in 150 milliliters of water where then added to the bowl. The resulting solution was then stirred rapidly with an electric mixer for one minute. The foam height in millimeters was then measured. The number of dishes which the solution could wash was determined by mixing equal volumes of Mazola Oil and Wesson Oil, adding 6 drops of mixture of the test solution and stirring rapidly with a mixer for one minute. The procedure was then repeated until the foam broke or until oil appeared on the surface of the water. One dish was equal to 6 drops of the oil mixture and the total number of dishes washed was equivalent to the number of 6 drop increments. The test compositions contained 20% sodium dodecyl benzene sulfonate, 6% sodium xylene sulfonate and, in the case of 1,3,4-tridecanetriol, 1% of the compound tested. With the 1,2,3-triol, preliminary foam stabilizer testing results appeared mediocre, so in the runs reported below 3%$_{wt.}$ 1,2,3-triol was employed. The control contained 20% sodium dodecyl benzene sulfonate and 6% sodium xylene sulfonate.

TABLE I

COMPARATIVE EVALUATION OF 1,2,3-DODECANETRIOL AND 1,3,4-TRIDECANETRIOL FOR DISHWASHING PERFORMANCE

| Ingredient | A | B | C |
|---|---|---|---|
| Sodium dodecylbenzene sulfonate | 20 | 20 | 20 |
| Sodium xylene sulfonate | 6 | 6 | 6 |
| 1,2,3-dodecanetriol | — | — | 3 |
| 1,3,4-tridecanetriol | — | 1 | — |
| Total | 26 | 27 | 29 |
| Performance at 0.06% | | | |
| Initial foam ht., mm. | 50 | 70 | 40 |
| Total dishes | 5 | 3 | 3 |
| Performance at 0.12% | | | |
| Initial foam ht., mm. | 80 | 90 | — |
| Total dishes | 10 | 21 | — |

From Table I it will be seen that at 0.06% concentration of the detergent composition the 1,3,4-triol-containing composition washed as many dishes as one containing 3 times as much of the 1,2,3-triol. No data was taken for the latter triol at 0.12% concentration in view of the relatively high degree of 1,2,3-triol insolubility in the testing composition. That composition required heating to 160° F. to clear, on cooling displayed a cloud point of about 120° F., and separated on further cooling. The relatively insoluble 1,2,3-triol, it should be noted, produced less foam than the control, from which it would appear the triol acts as an oil or soil, interfering with foam height. In view of the structural similarity of 1,2,3-dodecanetriol and 1,3,4-tridecanetriol, the relative insolubility of the former is indeed surprising.

EXAMPLE 3

Four additional linear aliphatic 1,3,4 triols were prepared from the corresponding 3-alken-1-ols by the method described in example 1. The isolation and purification steps were modified in progressing upward from $C_4$ through $C_9$ and $C_{11}$ to $C_{15}$ triols because of decreasing water solubility with increasing chain length. The butanetriol and nonanetriol were more difficult to isolate and purify from accompanying water soluble salts because their high water solubility prevented a drowning step. Recrystallization from methanol proved feasible. The three higher triols ($C_{11}$, $C_{13}$, $C_{15}$) were easily recovered by water drowning and recrystallization from hot water or acetone. Further purification, where indicated, was accomplished by petroleum ether deoiling of the flake product triols to remove any traces of olefinic alcohols. In Table II are listed various process and product parameters for the five triols prepared here including the good surface activity displayed by several of these compounds.

TABLE II
PHYSICAL PROPERTIES OF LINEAR, ALIPHATIC 1,3,4-TRIOLS

| Olefinic Alcohol | Product Triol | Crystalline Appearance | m.p.,° C | Sol. in Water At R.T.(approx) | Surface Tension, (dynes/cm 0.1%conc.) |
|---|---|---|---|---|---|
| 3-Buten-1-ol | 1,3,4-Butanetriol | Salt-Like | 200 | Complete | 71 |
| 3-None-1-ol | 1,3,4-Nonanetriol | Dry Powder | 200 | 10% | 57 |
| 3-Undecen-1-ol | 1,3,4-Undecanetriol | Soft Wax | 81–84 | 0.3% | 36 |
| 4-Tridecen-1-ol | 1,3,4-Tridecanetriol | Smooth Wax | 88.5–90 | 0.01% | 39(0.01%) |
| 3-Pentadecen-1-ol | 1,3,4-Pentadecanetriol | Hard Wax | 88–91 | Insoluble | — |

EXAMPLE 4

This example describes the evaluation of the detergent and foam boosting properties of selected members of the alkanetriol series. Performance was measured by means of the standard dishwashing test of Example 2. The control contained 20% sodium dodecylbenzene sulfonate and 6% sodium xylene sulfonate. The triol blends contained the components of the control plus 1% triol. The following data was taken:

TABLE III

| Composition | Concentration, (%) | Initial Foam Height (mm) | Total Dishes |
|---|---|---|---|
| Control | 0.06 | 50 | 5 |
|  | 0.12 | 80 | 10 |
| 1,3,4-Nonanetriol | 0.06 | 50 | 6 |
|  | 0.12 | 85 | 14 |
| 1,3,4-Undecanetriol | 0.06 | 70 | 10 |
|  | 0.12 | 90 | 22 |
| 1,3,4-Tridecanetriol | 0.06 | 70 | 3 |
|  | 0.12 | 90 | 21 |
| 1,3,4-Pentadecanetriol | 0.06 | 20 | 4 |
|  | 0.12 | 45 | 8 |

EXAMPLE 5

This example describes the preparation of a useful alkyd type resin formed by reaction of 350 parts by weight of the $C_9$ triol with 445 parts by weight of phthalic anhydride. The mixture of powdered ingredients formed a clear melt at about 50° C. On continued heating at 100°–110° C. over several hours the viscosity increased until a clear stringy polymer formed. A toluene solution of this material applied to a wooden surface formed a smooth clear adherent varnish-like coating.

A similar reaction with maleic anhydride (296 parts) and the $C_9$ triol (350 parts) yielded a toluene-insoluble polymer which was soluble in methylal, from which solution it was applied to a wooden surface to form a desirable coating.

EXAMPLE 6

This example illustrates the preparation of a foamed urethane polymer by warming a mixture of 35 parts of 1,3,4-nonadecanetriol with 55 parts of tolylene-2,4-diisocyanate. A voluminous foam formed quickly, and hardened into a solid expanded polymer strong enough to support its own weight and the weight of the reaction beaker in which it was prepared.

EXAMPLE 7

This example describes the preparation of a synthetic lubricating oil by the gradual addition of 32 parts of adipoyl chloride to 35 parts of 1,3,4-nonadecanetriol dissolved in 100 parts of pyridine. The stirred reaction mixture thickened and after 30 minutes 12 parts of octanoyl chloride were added. The product was drowned in aqueous hydrochloric acid. After water washing and drying a clear colorless oil of about SAE 10 viscosity and exhibiting desirable lubricant properties was obtained.

EXAMPLE 8

This example describes the complete esterification of 1,3,4-butanetriol (106 parts) with 490 parts of octanoyl chloride in the presence of pyridine to form a compound suitable as a synthetic lubricant. The yellow oily product (predominantly 1,3,4-butanetrioctoate), after water washing and drying, had $nD^{25}1.4540$.

Having described our invention with emphasis upon the preferred embodiments thereof, we wish it understood that the invention is not limited thereto, but only to the lawful scope of the appended claims.

We claim:

1. A 2 to about a 20 mole ethoxylate of a compound of structure:

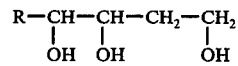

wherein R is a linear alkyl group of from about 5 to 9 carbon atoms, ethoxyl groups stemming from plural carbons of said compound.

2. A compound according to claim 1 wherein R is a linear alkyl group of 5 carbon atoms.

3. A compound according to claim 1 wherein R is a linear alkyl group of 7 carbon atoms.

4. A compound according to claim 1 wherein R is a linear alkyl group of 9 carbon atoms.

5. a 2 to about a 4 mole ethoxylate of the compoound of claim 2.

6. A 2 to about a 4 mole ethoxylate of the compound of claim 3.

7. A 2 to about a 4 mole ethoxylate of the compound of claim 4.

* * * * *